US011946570B2

(12) United States Patent
Béguin et al.

(10) Patent No.: US 11,946,570 B2
(45) Date of Patent: Apr. 2, 2024

(54) FLUID CHECK VALVE AND FLUIDIC SYSTEMS FOR GAS VENTING

(71) Applicant: Haemograph Pty Ltd, Bayswater (AU)

(72) Inventors: Steve Michaël Béguin, Bayswater (AU); Alexander Samuel Lubansky, Bayswater (AU); Jonathon Luke Miegel, Bayswater (AU); Paul Randall Stoddart, Bayswater (AU)

(73) Assignee: Haemograph Pty Ltd, Bayswater (AU)

( * ) Notice: Subject to any disclaimer, the term of this patent is extended or adjusted under 35 U.S.C. 154(b) by 220 days.

(21) Appl. No.: 17/638,270

(22) PCT Filed: Aug. 28, 2020

(86) PCT No.: PCT/AU2020/050902
§ 371 (c)(1),
(2) Date: Feb. 25, 2022

(87) PCT Pub. No.: WO2021/035305
PCT Pub. Date: Mar. 4, 2021

(65) Prior Publication Data
US 2022/0260181 A1    Aug. 18, 2022

(30) Foreign Application Priority Data
Aug. 28, 2019   (AU) .............................. 2019903149

(51) Int. Cl.
*F16K 99/00*    (2006.01)
*A61M 5/38*    (2006.01)
(Continued)

(52) U.S. Cl.
CPC ........... *F16K 99/0021* (2013.01); *A61M 5/38* (2013.01); *A61M 5/385* (2013.01); *A61M 39/24* (2013.01);
(Continued)

(58) Field of Classification Search
CPC ...... F16K 99/0021; F16K 13/10; F16K 24/04; F16K 2099/0086; A61M 5/38;
(Continued)

(56) References Cited

U.S. PATENT DOCUMENTS 4,031,891 A      6/1977 Jess
4,057,052 A *   11/1977 Kaufman ......... A61B 5/150236
                                                                604/125
(Continued)

FOREIGN PATENT DOCUMENTS

EP          0992257 A1     4/2000

OTHER PUBLICATIONS

International Search Report and Written Opinion in corresponding Application No. PCT/AU2020/050902, dated Nov. 6, 2020 (8 pages).
(Continued)

*Primary Examiner* — John Bastianelli
(74) *Attorney, Agent, or Firm* — Bookoff McAndrews, PLLC (57) ABSTRACT

A fluid check-valve for venting gas from a fluidic system comprises a retention body defining a fluid aperture having an upstream side and a downstream side, a hydrophilic porous material held by the retention body and disposed to cover the fluid aperture, and a hydrophobic porous material held by the retention body and disposed to cover the fluid aperture and adjacent the hydrophilic porous material. One face of the hydrophilic porous material is in fluid communication with the upstream side of the aperture, and one face of the hydrophobic porous material is in fluid communication with the downstream side of the aperture. The hydrophilic porous material is configured to retain liquid from the upstream side to hinder passage of gas from the downstream side to the upstream side, and the hydrophobic porous
(Continued)

material is configured to hinder passage of liquid from the upstream side to the downstream side.

21 Claims, 5 Drawing Sheets (51) Int. Cl.
*A61M 39/24* (2006.01)
*B01D 35/153* (2006.01)
*F16K 13/10* (2006.01)
*F16K 24/04* (2006.01)
*G01N 33/49* (2006.01)
*A61M 5/31* (2006.01)

(52) U.S. Cl.
CPC ............ B01D 35/153 (2013.01); F16K 13/10 (2013.01); F16K 24/04 (2013.01); G01N 33/49 (2013.01); *A61M 2005/3128* (2013.01); *A61M 2205/7527* (2013.01); *A61M 2205/7536* (2013.01); *B01D 2201/167* (2013.01); *F16K 2099/0086* (2013.01)

(58) Field of Classification Search
CPC .................. A61M 5/385; A61M 39/24; A61M 2005/3128; A61M 2205/7527; A61M 2205/7536; B01D 35/153; B01D 2201/167; G01N 33/49
USPC ........................................................ 137/803
See application file for complete search history.

(56) References Cited

U.S. PATENT DOCUMENTS

| | | | | |
|---|---|---|---|---|
| 4,244,379 A | * | 1/1981 | Smith | ............... A61B 5/150221 137/845 |
| 4,361,155 A | * | 11/1982 | Anastasio | ........ A61B 5/150503 600/576 |
| 4,571,244 A | | 2/1986 | Knighton | |
| 6,689,278 B2 | | 2/2004 | Beplate | |
| 7,097,690 B2 | * | 8/2006 | Usher | .................. A61M 5/1408 604/9 |
| 7,927,563 B1 | * | 4/2011 | Lavi | .................. A61B 5/150221 422/549 |
| 8,382,712 B2 | | 2/2013 | Kim | |
| 8,444,933 B2 | | 5/2013 | Kim et al. | |
| 2003/0042211 A1 | | 3/2003 | Beplate | |
| 2004/0178135 A1 | | 9/2004 | Beplate | |
| 2008/0312576 A1 | | 12/2008 | McKinnon et al. | |
| 2009/0326457 A1 | | 12/2009 | O'Connor | |
| 2013/0331787 A1 | | 12/2013 | Kraus | |
| 2014/0305196 A1 | * | 10/2014 | Ellis | ................... A61B 5/15105 210/321.72 |

OTHER PUBLICATIONS

International Extended Search Report in corresponding Application No. PCT/AU2020/050902, dated Jul. 31, 2023 (9 pages).

* cited by examiner

FLUID CHECK VALVE AND FLUIDIC SYSTEMS FOR GAS VENTING

CROSS-REFERENCE TO RELATED APPLICATIONS

This application is the U.S. national phase entry under 35 U.S.C. § 371 of International Application No. PCT/AU2020/050902, filed on Aug. 28, 2020, which claims priority to Australian Patent Application No. 2019903149, filed on Aug. 28, 2019.

TECHNICAL FIELD

The present disclosure generally relates to venting and sealing fluidic systems. More specifically, the present disclosure relates to check-valves for venting gas from fluidic systems while hindering outflow of liquid.

BACKGROUND

It is useful in some situations to selectively allow fluids to be removed from a vessel or channel system and to then prevent fluids from re-entering the region. For example, this may be achieved using one or more valves, such as check valves, safety valves and/or pressure relief valves. These valves are typically mechanical valves which may be fabricated from a metal, such as steel or brass. As such, they are not easily miniaturised and typically larger than 5 mm in diameter.

Additionally, there are some applications where it is necessary or desirable to selectively allow gases to be removed from the system while retaining liquids within the system. For example, it may be necessary to remove oxygen from a system to prevent oxidation of the remaining liquid. One approach to address this need is to evacuate the system and then seal the system. However, evacuation of a system may be undesirable or impractical due to the use of a vacuum pump, valves and/or a gas manifold.

Microfluidic systems typically involve the motion of liquids in channels with widths that are less than 3 mm. In this context, when a liquid is being loaded in a fluid line (or conduit), the gas is typically evacuated simultaneously via an outlet or a venting port. In the case of dead-ended fluidic systems, venting may be performed by diffusion of air through a permeable material such as polydimethylsiloxane (PDMS).

Due to the small size of microfluidic channels, the presence of bubbles in the fluid line may have significant impact on the system. Bubbles may disturb the optical properties of a system due to the mismatch of the refractive index of air and that of the liquid which may be important in some applications. Presence of air in undesired areas of a device may be detrimental to the processes at play. For example, air bubbles in a micro-bioreactor may lead to a cell being dried up and dying. In systems where a precise uniform flow control is necessary, it is critical to have the fluid line completely filled with the desired liquid. Local decrease of effective fluidic cross-section caused by a bubble in a channel may disturb the system by locally increasing the flowrate, shear rate and pressure drop. For those reasons, the effective removal of air bubbles in microfluidic systems is often necessary.

It may be desirable to obtain a rapid evaluation of the rheological properties of a patient's blood. Knowledge of such rheological properties is of value in assessing the administration of coagulants and anticoagulants to patients. It may also predict the likelihood of a bleed or thrombotic event in those that have a propensity to bleed or are at increased risk of clotting. Further situations in which it is important to know the rheological properties of blood include monitoring patients during surgery and during the reversal of anti-coagulation following surgery. Changes in blood rheology also occur in patients with sepsis and may provide an early indication that the condition is present. If sepsis is detected sufficiently early, treatment for the condition may be relatively straightforward.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Some embodiments relate to a fluid check-valve for venting gas from a fluidic system, the fluid check-valve comprising:
- a retention body defining a fluid aperture having an upstream side and a downstream side;
- a hydrophilic porous material held by the retention body and disposed to cover the fluid aperture;
- a hydrophobic porous material held by the retention body and disposed to cover the fluid aperture and adjacent the hydrophilic porous material,
- wherein one face of the hydrophilic porous material is in fluid communication with the upstream side of the aperture, and one face of the hydrophobic porous material is in fluid communication with the downstream side of the aperture, and
- wherein the hydrophilic porous material is configured to retain liquid from the upstream side to hinder passage of gas from the downstream side to the upstream side, and the hydrophobic porous material is configured to hinder passage of liquid from the upstream side to the downstream side.

The hydrophilic porous material may be disposed upstream of the hydrophobic porous material.

The at least one of the hydrophilic porous material and the hydrophobic porous material may define a plurality of pores, and the plurality of pores have a median pore diameter in the range of about 0.1 microns to about 10 microns. In some embodiments, the plurality of pores have a median pore diameter less than about 1 micron. The hydrophilic porous material may define a plurality of first pores having a median second pore size less than about 0.5 microns. The hydrophobic porous material may define a plurality of second pores having a median second pore size less than about 0.3 microns.

The hydrophobic porous material and the hydrophilic porous material directly contact each other. In some embodiments, the hydrophobic porous material and the hydrophilic porous material are spaced from each other. The hydrophobic porous material and the hydrophilic porous material may be spaced from each other by a distance greater than about 0 mm and less than about 2 mm. The hydrophobic porous material and the hydrophilic porous material may be separated by a material that allows the passage or transmission of fluid. In some embodiments, the hydrophobic porous material and the hydrophilic porous material are separated by a void.

The retention body may comprise a first part and a second part, wherein the first part and second part are coupled together to cooperatively retain the hydrophilic porous material and the hydrophobic porous material. The first part and second part may be: shaped to form a friction fit, or bonded together.

One of the first part and second part may be shaped to define a recess and a section of the other of the first and second parts is shaped to fit within the recess such that the first part and second part are coupled together. The recess may have a size that is tapered along a depth of the recess. At least a section of each of the hydrophilic porous material and the hydrophobic porous material may be located within the recess.

The first part may comprise an upstream surface in fluid connection with the upstream side that has at least a portion of a frustoconical or a concave shape to assist passage of gas from the upstream side to the downstream side.

The hydrophilic porous material may comprise a hydrophilic membrane. The hydrophobic porous material may comprise a hydrophobic membrane. In some embodiments, the hydrophobic membrane and/or the hydrophilic membrane comprises a polytetrafluoroethylene substrate.

The hydrophilic porous material may comprise a hydrophilic coating. The hydrophobic porous material may comprise a hydrophobic coating.

If the hydrophilic porous material has been exposed to a liquid, the fluid check-valve may hinder the passage of gas from the downstream side to the upstream side with a backflow pressure limit of about −80 kPa.

The hydrophobic porous material may be configured to hinder the passage of liquid from the upstream side to the downstream side with a leakage pressure limit of about 250 kPa. In some embodiments, the hydrophobic porous material is configured to hinder the passage of liquid from the upstream side to the downstream side with a leakage pressure limit of about 150 kPa. In some embodiments, the hydrophobic porous material is configured to hinder the passage of liquid from the upstream side to the downstream side with a leakage pressure limit of about 100 kPa.

Some embodiments relate to a self-sealing venting fluidic system comprising:
  a fluid conduit comprising an inner surface; and
  a fluid check-valve as described herein, wherein the fluid check-valve is fitted within the fluid conduit and forms a fluidic seal with the inner surface of the fluid conduit to separate the fluid conduit into an upstream side to contain a gas and a liquid, and a downstream side to receive the gas.

The fluid conduit may define a plurality of ports in fluid communication with the upstream side to enable pressure measurements to be performed. The fluid conduit may define an inlet in fluid communication with the upstream side to enable fluids to be injected into the upstream side.

The fluidic system may further comprise a plunger adapted to fit within the fluid conduit, wherein the plunger comprises the fluid check-valve. The fluidic system may further comprise an automated motion control system configured to engage the plunger to control the movement of the plunger.

In some embodiments, the fluidic system further comprises a baffle component located within the fluid conduit adjacent to the first part to promote liquid flow along the inner surface of the fluid conduit.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments are described in further detail below, by way of example, with reference to the accompanying drawings briefly described below.

DESCRIPTION OF EMBODIMENTS

The present disclosure generally relates to venting and sealing fluidic systems. More specifically, the present disclosure relates to check-valves for venting gas from fluidic systems while hindering outflow of liquid.

A microfluidic device may be used to measure rheological properties of blood. The present applicant's earlier filed patent application PCT/GB2017/053393 discloses an example of such a device. By controlling the flow rate of a sample fluid within a measurement section of the device, viscosity and shear rate can be calculated from a suitable fluidic device. For example, the fluidic device may comprise a pumping apparatus to control the flowrate of the sample flowing in the measurement unit where the pressure drop in a channel of defined dimensions is measured. With a known pressure drop, a known flow rate, and known channel dimensions, the viscosity and shear rate can be calculated. The flowrate is controlled via a syringe pump and the pressure drop across the measurement channel is performed using differential pressure sensors. To measure the full spectrum of viscosity properties of non-Newtonian fluids such as blood (i.e. that vary with the shear rate), the flowrate may be varied progressively over time following a sinusoidal pattern.

However, if a gas bubble gets trapped in the fluidic system between the syringe and the measurement channel, the gas bubble would get compressed and de-compressed due to the change in flowrate applied and subsequent variable pressure experienced throughout the fluid line. The bubble would therefore have its volume decreased and increased due to the pressure change. In turn, this would introduce a significant difference between the flowrate imposed by the movement of the syringe pump and the actual flowrate of the sample passing in the fluid line where the pressure difference is measured. Since the flowrate considered in the calculation of the viscosity is defined solely by the movement of the piston of the syringe pump, the aforementioned difference in flowrate between volumetric change in the syringe and the flowrate of the liquid in the channel where the pressure is measured generates an unacceptable error in the calculated viscosity. This error would therefore invalidate the measurement. Additionally, if a bubble is trapped within the measurement portions of a channel, less liquid than expected would be measured and/or the effective cross-section of the channel would be reduced. This creates significant errors in the calculated viscosity and/or invalidate calculations for the viscosity that use the physical/absolute cross-sectional size of the channel. This highlights the importance of removing bubbles from the system.

Figure 1:
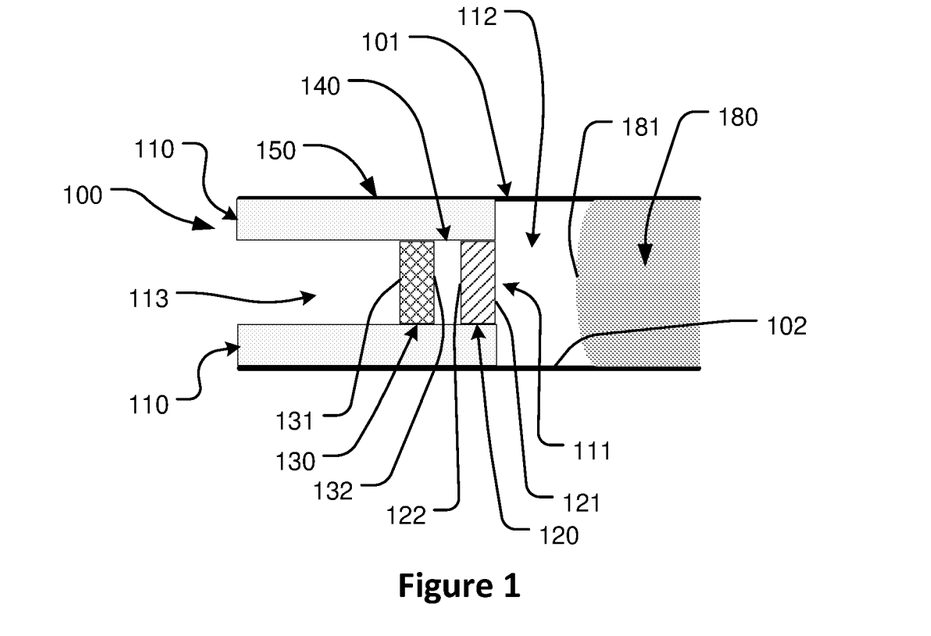
FIG. 1 is a schematic diagram in side cross-section of a valve component according to some embodiments.

Referring to FIG. 1, a fluid check-valve 100 for venting gas from a fluid conduit 101 is shown. The fluid check-valve 100 comprises a retention body 110 defining a fluid aperture 111 having an upstream side 112 and a downstream side 113.

The fluid check-valve 100 also comprises a hydrophilic porous material 120 held by the retention body 110 and disposed to cover the fluid aperture 111; and a hydrophobic porous material 130 held by the retention body 110 and disposed to cover the fluid aperture 111 that is adjacent to the hydrophilic porous material 120. The hydrophilic porous material 120 is positioned upstream of the hydrophobic porous material 130.

One face 121 of the hydrophilic porous material 120 is in fluid communication with the upstream side 112 of the aperture 111, and one face 131 of the hydrophobic porous material 130 is in fluid communication with the downstream side 113 of the aperture 111.

The hydrophilic porous material 120 is configured to retain liquid from the upstream side 112 to hinder passage of gas from the downstream side 113 to the upstream side 112. The hydrophobic porous material 130 is configured to hinder passage of liquid from the upstream side 112 to the downstream side 113.

If the upstream side 112 of the fluid conduit 101 initially comprises only (or predominantly) gas, and a liquid 180 is injected into the upstream side 112 fluid conduit 101 the liquid comprises a liquid surface 181 that may push the gas out of the upstream side 112 through aperture 111, the hydrophilic porous material 120 and the hydrophobic porous material 130, such that the gas passes through to the downstream side 113. As liquid 180 proceeds to be injected into the upstream side 112, the liquid surface 181 and liquid 180 may enter and be retained by the hydrophilic porous material 120. The hydrophilic porous material 120 with retained liquid 180 hinders and/or prevents the passage of gas through the hydrophilic porous material 120. The hydrophilic porous material 120 may, for example, have a strong capillary pressure to assist in retaining high surface tension liquids inside its mesh.

In some embodiments, the retained liquid 180 is difficult to remove from the hydrophilic porous material 120. The fluid check-valve 100 may therefore be considered a single-use check-valve as gas can practically only be vented until the hydrophilic porous material 120 retains the liquid 180 and hinders or prevents further gas venting. However, if the liquid 180 is removed from the hydrophilic porous material 120 (e.g. by evaporation, heating or otherwise drying the hydrophilic porous material 120) then the fluid check-valve 100 can be reused.

After liquid has entered the hydrophilic porous material 120, at least some of the liquid 180 may pass through hydrophilic porous material 120 and enter the space (or void) created by a gap 140 and/or contact the hydrophobic porous material 130. However, the liquid 180 is hindered from passing through the hydrophobic porous material 130. The hydrophobic porous material 130 may have a strong repelling pressure that inhibits high surface tension liquids from entering its mesh. The hindrance of liquid 180 through the hydrophobic porous material 130 (or fluidic resistance of the hydrophobic porous material 130 to the passage of liquid 180 therethrough) may be due to the degree of hydrophobicity of the hydrophobic porous material 130, pore sizes in the hydrophobic porous material 130 and the surface tension of the particular liquid 180 being measured/tested. This minimises the loss of fluid from the fluidic system 200, and the amount of fluid needed to operate the fluidic system 200 is thereby reduced. This advantageously reduces the costs involved with reagents and minimise the amount of blood sample required for measurements. The ability of the hydrophobic porous material 130 to allow gases to pass therethrough exploits the difference in viscosity between the gases and liquid 180.

The hydrophobic porous material 130 may, for example, be particularly suitable for hindering the passage of polar liquids. The liquid 180 to be retained by the fluid check valve 100 may include any one or more of: a non-Newtonian fluid, blood (whole), blood serum, and blood plasma.

The fluid check-valve 100 does not comprise moving parts. This advantageously improves its reliability and may reduce its manufacturing costs. The simplicity of its design also enables it to be fabricated at dimensions suitable for micro-fluidic applications. The fluid check-valve 100 may, for example, be sized to be fitted within a micro-fluidic channel of a fluid conduit 101. The exposed area of the fluid check valve 100 may be equivalent in area to a circle with a diameter less than about 3 mm. The total area of the fluid check-valve 100 exposed to fluid from the upstream side 112 may be between about 0.4 $mm^2$ and about 10 $mm^2$. However, in some embodiments, the total area of the fluid check-valve 100 exposed to fluid from the upstream side 112 is between about 0.01 $mm^2$ and about 100 $mm^2$. In some embodiments, the total area of the fluid check-valve 100 exposed to fluid from the upstream side 112 is between about 0.4 $mm^2$ and about 80 $mm^2$. The total area of the fluid check-valve 100 exposed to fluid from the upstream side 112 may be between about 0.4 $mm^2$ and about 20 $mm^2$.

The area of the aperture 111 may be less than the exposed area of the fluid check-valve 100.

Both the hydrophilic porous material 120 and the hydrophobic porous material 130 may be arranged 'in-line' between the upstream side and the downstream side to cooperatively hinder (or restrict) passage of gas from the downstream side 113 (if the hydrophilic porous material 120 retains liquid) and hinder passage of liquid from the upstream side 112. The hydrophilic porous material 120 may be disposed upstream of the hydrophobic porous material 130.

The hydrophilic porous material 120 and the hydrophobic porous material 130 may be arranged such that the hydrophobic porous material 130 is in fluid connection with the upstream side 112 via the hydrophilic porous material 120

The hydrophilic porous material 120 may define a plurality of pores (not shown) with a distribution of pore sizes. The median diameter of the pores (first pores) may be larger than about 2 nm. In some embodiments, the first pores of the hydrophilic porous material 120 have a median diameter in the range of about 2 nm to about 10 microns. The hydrophilic porous material 120 may comprise an ultra-filtration (or nano-porous) filter. In some embodiments, the first pores of the hydrophilic porous material 120 have a median diameter in the range of about 0.1 microns to about 10 microns. In some embodiments, the first pores of the hydrophilic porous material 120 have a median diameter in the range of about 0.2 microns to about 1 micron. The first pores of the hydrophilic porous material 120 may have a median diameter of about 0.5 microns such as 0.45 microns.

Although surfaces of the hydrophilic porous material 120 have an affinity for the liquid 180, the porous structure of the hydrophilic porous material 120 may also hinder the passage of liquid 180 therethrough because of surface tension in the liquid 180. However, if the pressure is above a threshold pressure, liquid 180 may pass into the hydrophilic porous material 120 to be retained therein. The threshold pressure may, for example be about 25 kPa where the largest pores have a size equivalent to a circle with a diameter of about 0.45 microns.

If the hydrophilic porous material 120 has retained liquid within the plurality of pores across the aperture 111 to thereby clog or block the pores and form at least part of a hermetic seal, then the hydrophilic porous material 120 (and therefore the check-valve 100) may substantially prevent passage of gas from the downstream side 113 to the upstream side 112 up to a pressure limit (leak or back-flow pressure limit). The back-flow pressure limit is a negative pressure limit on the upstream side 112 relative to the downstream side 113. The back-flow pressure limit may be about −100 kPa (meaning pressures <−100 kPa or a negative pressure with a magnitude greater than the back-flow pressure limit would lead to a gas leak into the upstream side 112). In some embodiments, the back-flow pressure limit may be about −80 kPa.

It is understood that the pore size affects the back-flow pressure limit along with the affinity that the hydrophilic porous material has for the liquid to be retained. The hydrophilic porous material 120 may be selected with pore sizes of a particular size to achieve the back-flow pressure limit desired. For example, the following equation for capillary pressure may be used to determine the maximum pore size of radius r to achieve a specific back-flow pressure limit $P_L$:

$$P_L = \frac{2 \cdot \sigma \cdot \cos\theta}{r}$$

Where σ is the surface tension at an interface between liquid 180 and air, θ is the contact angle between a surface of the liquid 180 and a pore wall.

The seal between the hydrophilic porous material 120 and the retention body 110 also needs to withstand pressures up to at least the leak pressure.

If the hydrophilic porous material 120 has retained liquid within the plurality of pores across only a portion of the aperture 111, the passage of gas may be hindered but it may not be sufficiently hindered to form a hermetic seal and substantially prevent fluid (i.e. gas) flow from the downstream side 113 to the upstream side 112 up to the back-flow pressure limit.

The hydrophilic porous material 120 and the hydrophobic porous material 130 may be separated by a gap 140 where the distance between opposing faces of the hydrophilic porous material 120 and the hydrophobic porous material 130 may be less than about 2 mm. The gap 140 may be filled with a material (that may form a structure) that allows the passage or transmission of fluid, i.e. a fluid conductive material (not shown), a mechanical scaffolding or a filler material. The fluid conductive material may, for example, be a porous material with pores that have a diameter greater than about 5 microns. A fluid conductive material with pore sizes around 5 microns may let more fluid through to the hydrophobic porous material 130 compared to materials with smaller pores. This is generally undesirable but by using pore sizes around 5 microns this process of allowing fluid through to the hydrophobic porous material 130 may be advantageously faster and occur with lower operating pressures.

In some embodiments, the gap 140 is a void that may be filled with a gas or liquid or at least partially filled with a liquid. The gap 140 may be considered a 'dead volume'.

In some embodiments, the structure in the gap 140 may define a funnel (not shown) contracting in cross-sectional size and then increasing in cross-sectional size along a length of the funnel. The funnel may also comprise an intermediate tube length of fixed diameter. For example, the funnel may contract from a diameter of 3 mm to 1 mm over a length of 0.5 mm, then a 9 mm length tube of 1 mm diameter, then a funnel expanding back to 3 mm over a 0.5 mm length. This would be equivalent in dead volume to about 1 mm length at 3 mm diameter. The funnel spaces may be filled with a scaffolding material that would provide greater mechanical stability to the hydrophilic porous material 120 and the hydrophobic porous material 130 while reducing the volume available to the liquid, to further reduce the dead volume.

In some embodiments, the hydrophilic porous material 120 and/or the hydrophobic porous material 130 may arranged such that they have opposing surfaces 122, 132 that are not parallel with respect to each other. The opposing surfaces 122, 132 may also be generally non-planar and have a curved or undulating shape. In these situations the distance separating the hydrophilic porous material 120 and/or the hydrophobic porous material 130 is taken to be the largest distance between the opposing surfaces 122, 132.

In some embodiments, the hydrophilic porous material 120 and the hydrophobic porous material 130 directly contact each other. This eliminates the gap 140 and advantageously reduces the amount of space in the check valve 100 that may contain liquid that can flow back into the upstream side 112 if the upstream side is under a negative pressure relative to the downstream side 113. In some embodiments, the dead volume may be less than 1 micro-litre.

The hydrophobic porous material 130 may define a plurality of pores (not shown) with a distribution of pore sizes. The median diameter of the pores (second pores) may be larger than about 2 nm. In some embodiments, the second pores of the hydrophobic porous material 130 have a median diameter in the range of about 2 nm to about 10 microns. The hydrophobic porous material 130 may comprise an ultrafiltration (or nano-porous) filter. In some embodiments, the second pores of the hydrophobic porous material 130 have a median diameter in the range of about 0.1 microns to about 10 microns. In some embodiments, the second pores of the hydrophobic porous material 130 have a median diameter in the range of about 0.1 microns to about 0.5 microns. In some embodiments, the second pores of the hydrophobic porous material 130 have a median diameter in the range of about 0.1 microns to about 0.3 microns. For example, the second pores of the hydrophobic porous material 130 may have a median diameter of about 0.2 microns, such as a nominal diameter of 0.22 microns.

The hydrophobic porous material 130 may have a strong repelling pressure hindering a high surface tension liquid from entering its mesh. Advantageously, pore sizes less than 10 microns enable the hydrophobic porous material 130 to hinder the passage of some liquids to the downstream side 113 up to a pressure limit (e.g. a burst or rupture pressure limit, or a leakage pressure limit) suitable for typical microfluidic operating conditions. The leakage pressure limit may be about 250 kPa (meaning pressure greater than 250 kPa leads to escape of liquid into the downstream side 113 through the hydrophobic porous material 130). In some embodiments, the leakage pressure limit may be about 150 kPa. In some embodiments, the leakage pressure limit may be about 100 kPa.

It is understood that the hydrophobic material affects the leakage pressure limit as well. For example, the membrane may be formed from a polymer such as polytetrafluoroethylene (PTFE) and have a leakage pressure limit of at least about 250 kPa. The seal between the hydrophobic porous material 130 and the retention body 110 also needs to withstand pressures up to the leakage pressure limit.

In some embodiments, either one or both of the hydrophilic porous material 120 and the hydrophobic porous material 130 may comprise a membrane. The membrane may, for example, form a substrate for the material. The membrane may comprise a mesh defining the pores. The membrane may, for example, be the same or similar to those found in commercially available syringe filters.

The hydrophilic porous material 120 may comprise a hydrophilic coating or layer on the substrate to form a hydrophilic membrane. The hydrophilic membrane may, for example, be the same or similar to those found in commercially available filters such as Nuclepore™ filters provided by Whatman, Virtek™ vents by Porex Filtration Group, and other filters provided by Sterlitech Corp., Advantec MFS Inc., and GVS S.p.A.

The hydrophilic porous material 120 may have a strong capillary pressure to keep a liquid (such as a high surface tension liquid) inside its pores and/or its mesh. The surface tension depends on the type of liquid 180 and the material that the hydrophilic porous material 120 is formed from. For example, if the liquid 180 comprises ethanol, then the hydrophilic porous material 120 may not work as well to hinder the passage of gas after the hydrophilic porous material 120 has retained the liquid 180. In another example, if the liquid 180 comprises hexane, then the liquid may not pass through into the hydrophilic porous material 120.

The hydrophobic porous material 130 may comprise a hydrophobic coating or layer on the substrate to form a hydrophobic membrane. The hydrophobic membranes may have a strong repelling pressure capable of hindering and/or preventing a liquid (such as a high surface tension liquid) from entering its pores and/or its mesh. The hydrophobic membrane may, for example, be the same or similar to those found in commercially available filters such as Nuclepore™ filters provided by Whatman, Virtek™ vents by Porex Filtration Group, and other filters provided by Sterlitech Corp., Advantec MFS Inc., and GVS S.p.A.

The fluid check-valve 100 may be configured (e.g. sized and shaped) so that it can fit and be located within the fluid conduit 101. The fluid check-valve 100 may comprise an outer surface 150 of the fluid that engages at least a portion of an inner surface 102 of the fluid conduit 101 to seal the fluid conduit 101 (create a fluidic seal) to separate the fluid conduit 101 into an upstream side 112, and a downstream side 113.

The seal formed between the check-valve 100 and inner surface 102 prevents gases from passing from the upstream side 112 to the downstream side 113 other than via the aperture 111. However, if the hydrophilic porous material 120 retains a liquid over the aperture 111, then gases are hindered or prevented from passing from the upstream side 112 to the downstream side 113.

Figure 2:
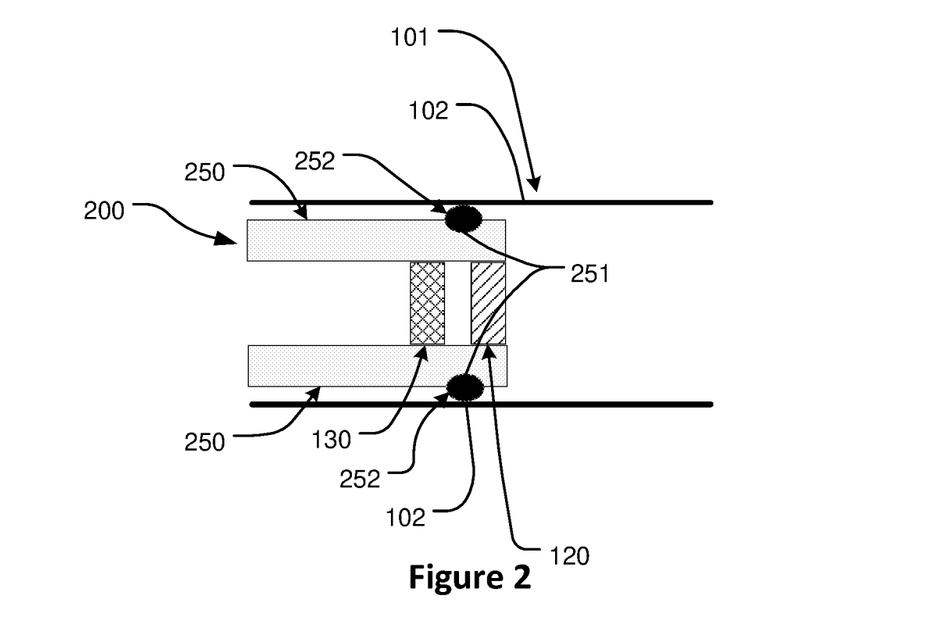
FIG. 2 is a schematic diagram in side cross-section of a valve component according to some embodiments.

Referring to FIG. 2, the check-valve 200 may further comprise a sealing member such as an O-ring 252. The sealing member may engage an outer surface 250 of the retaining body 210 and, when the check-valve 200 is located within the fluid conduit 101, the sealing member may also engage at least a portion of an inner surface 102 of the fluid conduit 101 to seal the fluid conduit 101 so that fluid can only pass from the upstream side 112 to the downstream side 113 via the aperture 111 and the fluid check-valve 100.

In some embodiments, the outer surface 250 of the retaining body 210 may define a recess or groove 251 to retain the sealing member. The recess or groove 251 may extend circumferentially around the retaining body 210.

Figure 3:
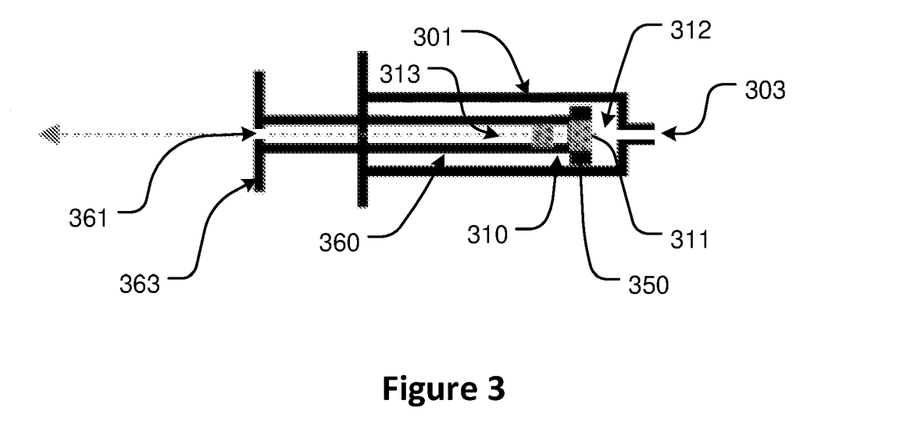
FIG. 3 is a schematic side view diagram of a fluidic system comprising a valve component according to some embodiments.

FIG. 3 shows a self-sealing venting fluidic system 300 comprising a fluid conduit 301 and a plunger 360 comprising a fluid check-valve 310. The plunger 360 and the fluid check-valve 310 are adapted to fit within the fluid conduit 301. When the plunger 360 is fit within the fluid conduit 301, an outer surface 350 of the plunger 360 engages an inner surface 302 of the fluid conduit 301 to seal the fluid conduit 301 and, along with the aperture 311, separates the fluid conduit 301 into an upstream side 312 and a downstream side 313. The fluidic seal between the inner surface 302 of the fluid conduit 301 separates the fluid conduit into an upstream side to contain a gas and a liquid, and a downstream side to receive the gas.

Advantageously, as the upstream side 312 is filled with a liquid (not shown), the fluid check-valve 310 allows: any gas within the upstream side 312 to vent out of the upstream side 312 and pass through to the downstream side 312; hinder or stop the liquid from passing through; and hinder or prevent any gas from passing back into the upstream side 312 from the downstream side 313.

The plunger 360 may define a venting path 361 in fluid connection with the downstream side 313 to guide gas that has passed from the upstream side 312 to the downstream side 313 to pass through and/or pass the plunger 361.

The plunger 360 may be configured to be displaced along the fluid conduit 301 while maintaining the seal with the fluid conduit 301. The outer surface 350 may, for example, be formed from a polymer material. The plunger 360 may therefore be actuated to force liquid in the upstream side 312 to move along the fluid conduit 301.

The plunger 360 may comprise a flange 363 to assist in the application of a force to the plunger 360 to displace the plunger 360.

The fluid conduit 301 may comprise a fluid outlet 303 so that the liquid may be forced out of the upstream side 312 by the plunger 360. As the fluid check-valve 100, 200, 310 allows gases to be removed from the upstream side 312 and prevents gas from re-entering the upstream side 312, the fluid system 300 may assist in providing accurate dispensing of the liquid.

Figure 4:
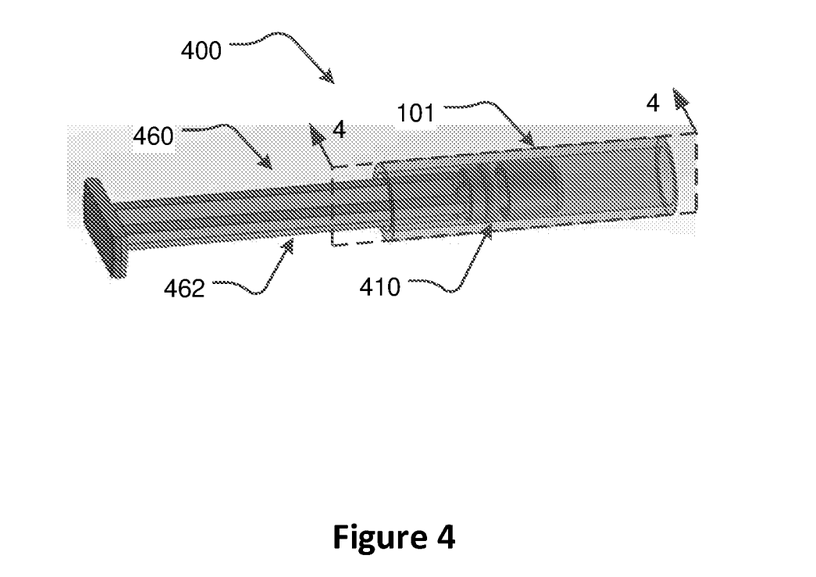
FIG. 4 is a perspective view of a fluidic system comprising a plunger comprising a valve component according to some embodiments.
Figure 5:
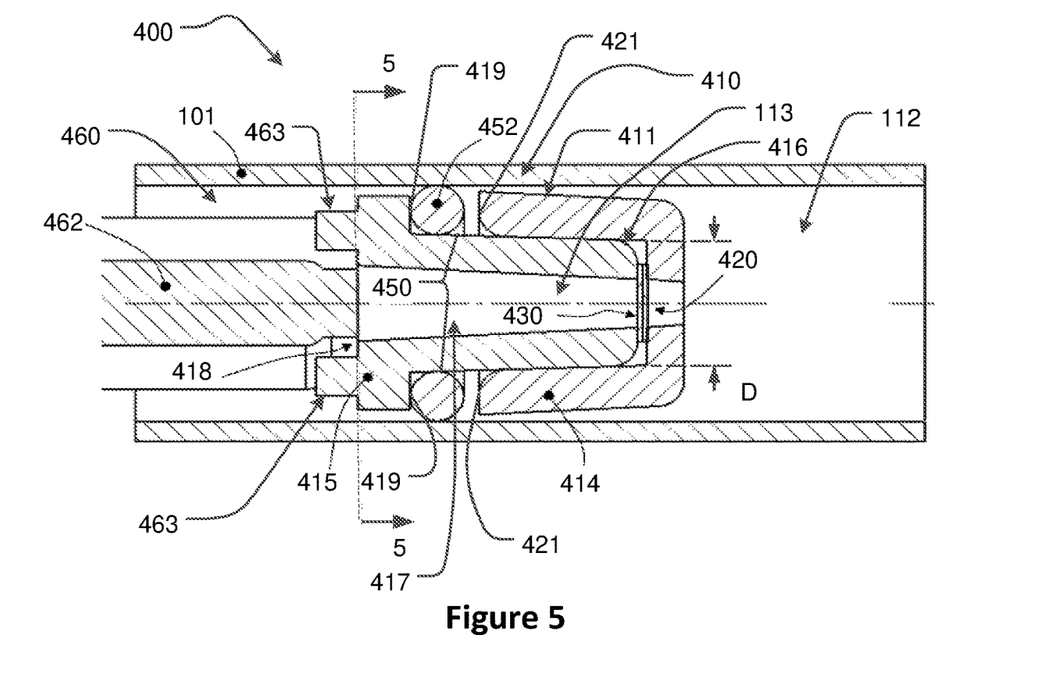
FIG. 5 is a cross-sectional view of the fluidic system of FIG. 4 along plane 4-4.
Figure 6:
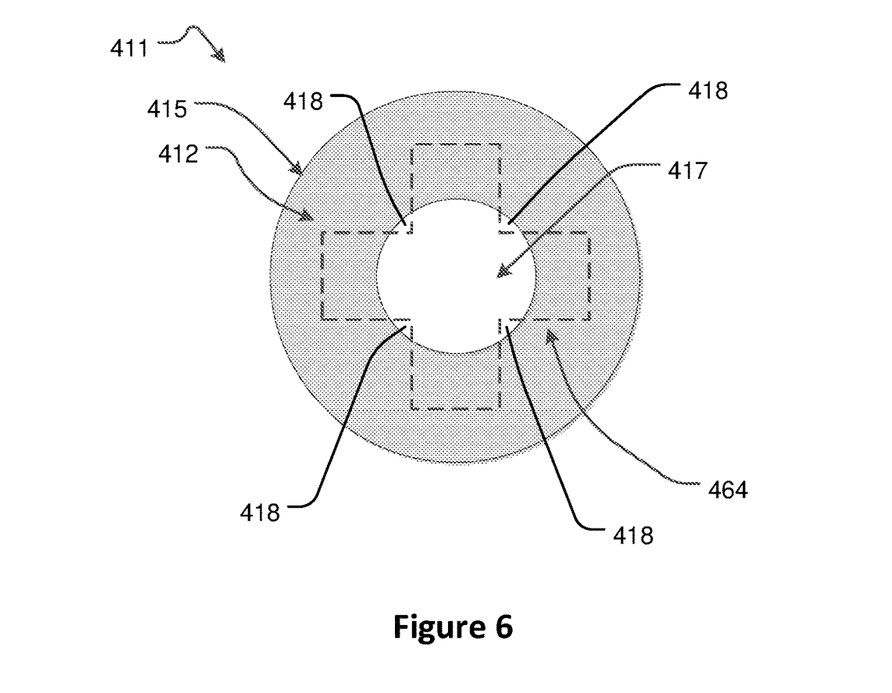
FIG. 6 is a cross-sectional view of the fluidic system of FIG. 4 along line 5-5.

FIGS. 4, 5 and 6 show a fluid system 400 comprising a fluid conduit 101 and a plunger 460 comprising a fluid check-valve 410 and a plunger stick 462. The fluid check-valve 100, 200, 310, 410 and at least a portion of the plunger stick 462 are adapted to fit within the fluid conduit 101.

The retaining body 411 may comprise a first part 414 and a second part 415. The first part 414 and second part 415 are configured to couple and/or interconnect with each other. Either one of the first part 414 or the second part 415 may be shaped to define a recess 416 that the other part is shaped to fit within. For example, the first part 414 may be shaped to define a recess 416 and the second part 415 may be shaped to fit within the recess 416.

The recess 416 and the other of the first part 414 or the second part 415 may have a transverse dimension such as a diameter D that is tapered along a depth of the recess 416. The recess 416 may, for example, have a frustoconical or frustopyramidal shape. In some embodiments, the recess 416 may not have a constant transverse dimension. For example, the recess may have a cylindrical, square or rectangular shape.

At least a part of (or all of) one or both of the hydrophilic porous material 420 and the hydrophobic porous material 430 may be located within the recess 416. In some embodiments, the first part 414 and a second part 415 are coupled and/or interconnected with each other to cooperatively retain the hydrophilic porous material 420 and the hydrophobic porous material 430.

In some embodiments, a friction fit is formed between the first part 414 or the second part 415. The shape of the recess 416 and the other of the first part 414 or the second part 415 may assist in forming a friction fit. The shape of the other of the first part 414 or the second part 415 may complement the shape of the recess 416.

In some embodiments, the first part 414 or the second part 415 are coupled together by any one of: chemical bonding, heat sealing and an adhesive. The first part 414 or the second part 415 may be either removably or fixably attached to each other.

In some embodiments, the hydrophilic porous material 420 and the hydrophobic porous material 430 may be retained by the retaining body 411 by applying pressure, pinching, imprinting and deformation of the materials 420, 430, fusing, ultrasonic welding, thermal welding, laser welding, overmolding, etc. Alternatively, the hydrophilic porous material 420 and the hydrophobic porous material 430 may be formed (e.g. injection molded) directly within one or more of first part 414 or the second part 415.

The fluid check-valve 410 may be retained by the plunger stick 462 by two or more tabs 463 on a downstream face 412 of the retaining body 411. The contacting face 464 of the plunger stick 462 may be shaped to complement the tabs 463 to engage the tabs 463.

The fluid check-valve 410 may comprise an inner conduit 417 defining a fluid passage on the downstream side 113 of the hydrophobic porous material 430. The transverse cross-sectional shape of the inner conduit 417 may be different to the contacting face 464 of the plunger stick so that vents 418 are defined that enable gas to escape from the inner conduit 417 when the fluid check-valve 410 is retained by the plunger stick 462.

The fluid check-valve 410 may comprise a flange 419 to retain an O-ring 452. For example, the second part 415 may comprise flange 419. The flange 419 may extend circumferentially around the second part 415. In some embodiments, the first part 414 may comprise a lip 421 to further retain the O-ring 452. The lip 421 may extend circumferentially around the second part 415 when interconnected with the first part 414. The flange 419, lip 421 and outer surface 450 of the second part 415 may collectively retain the O-ring 452.

Figure 7:
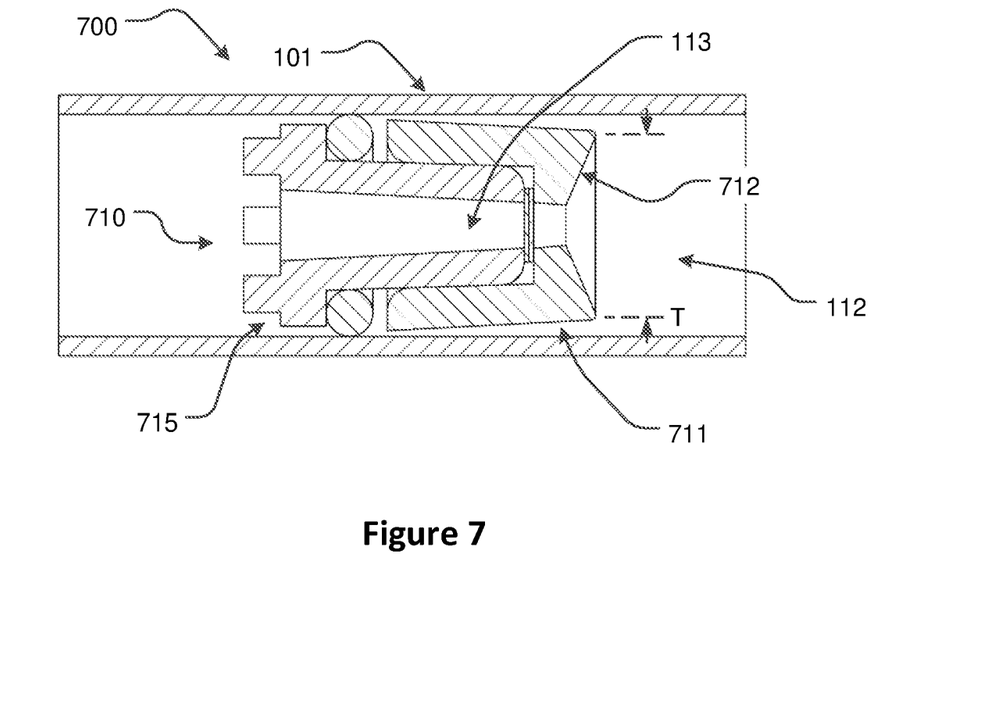
FIG. 7 is a cross-sectional view of a fluidic system comprising a valve component according to some embodiments.
Figure 8:
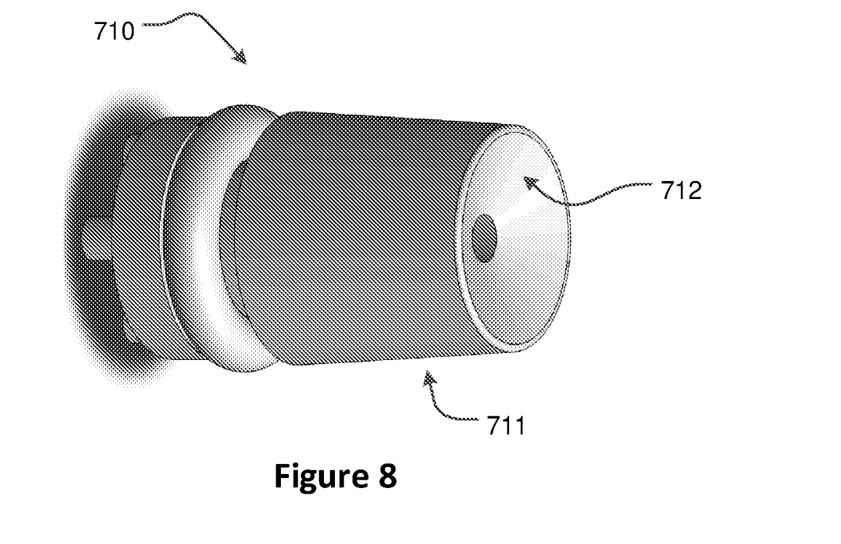
FIG. 8 is a perspective view of the valve component of FIG. 7.

Referring to FIGS. 7 and 8, a fluidic system 700 is shown comprising a fluid check-valve 710 within the fluid conduit 101. The fluid check-valve 710 comprises a first part 711 and a second part 415. The first part 711 may comprise an upstream surface 712 in fluid connection with the upstream side 112 of the fluid conduit 101 that has a transverse dimension T with a reducing size. For example, the upstream surface 712 may comprise at least a portion of a frustoconical, frustopyramidal or a concave shape to assist passage of gas from the upstream side 112 to the downstream side 113. The upstream surface 712 may have at least a portion of an inverse spherical shape.

In some embodiments, the fluidic system 300, 400, 700 may also comprise a structure (not shown) such as a baffle within the fluid channel defined by the fluid conduit 101 to promote liquid flow along the inner surface 102 of the fluid conduit 101 and reduce the risk of air bubbles being trapped on the upstream side 112 near the inner surface 102. The baffle may, for example, be either attached to the fluid conduit 101 or the fluid check-valve 100, 310, 410, 710.

In some embodiments, to reduce the risk of air bubbles being trapped near the inner surface 102 of the fluid conduit 101, the contact angle between the surface 181 of liquid 180 and the inner surface 102 of the fluid conduit 101 and/or fluid check-valve 100, 310, 410, 710 may be increased by forming the inner surface 102 of the fluid conduit 101 with a hydrophilic material and/or forming the retaining body 110 of the fluid check-valve 100, 310, 410, 710 with a hydrophobic material.

An inner surface 102 formed from a hydrophilic material (e.g. poly(methyl methacrylate), PMMA) may favour the establishment of a concave meniscus filling the fluid conduit 101 by the liquid 180.

In some embodiments, fluid check-valve 100, 310, 410, 710 (or at least the upstream surface 712) may be formed from or coated with a hydrophobic material (e.g. polyethylene, PE) to minimise premature wicking of the upstream surface 712 of the fluid check-valve 100, 310, 410, 710 which would otherwise lead to wetting the hydrophilic porous media 120 before complete gas venting.

Figure 9:
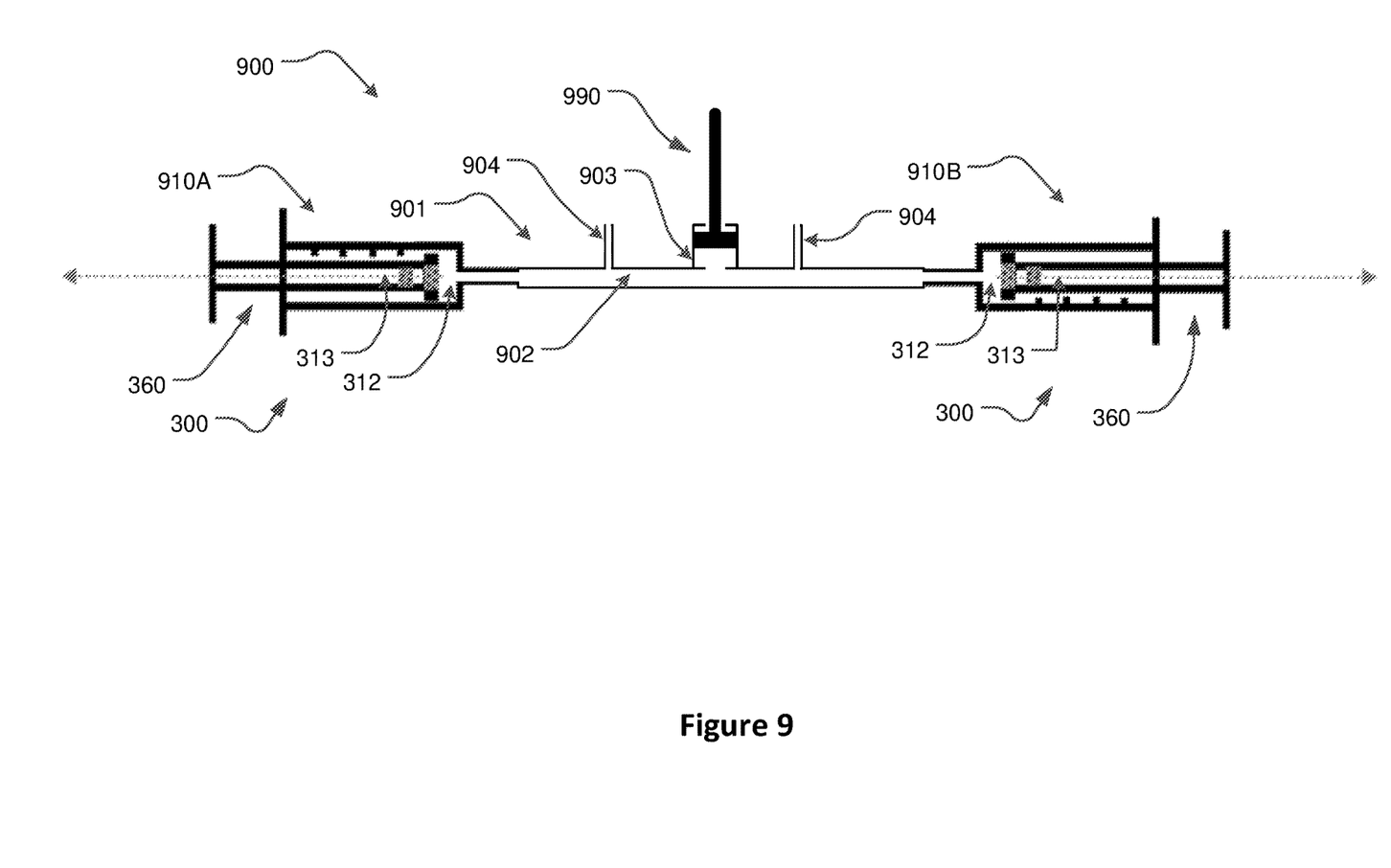
FIG. 9 is a schematic side view diagram of a fluidic system comprising a plurality of plungers according to some embodiments.

Referring to FIG. 9, a fluidic device 900 is shown comprising a fluid conduit 901 defining a channel 902, a first syringe 910A and a second syringe 910B. The first and second syringes 910A, 910B each comprise a fluidic system 300, 400, 700 as previously described. The upstream sides 112, 312 of the fluidic system 300, 400, 700 are in fluid connection with the channel 902. The fluid conduit 901 further comprises a fluid inlet 903. The fluid inlet 903 may be adapted to receive an inlet plunger 990 that may be used to force liquid through the channel 901 and the upstream sides 112, 312 of the fluidic system 300, 400, 700 to expel gas from the fluid conduit 901 via the downstream sides 113, 313.

The fluid conduit 901 comprises two or more ports 904 in fluid connection with the channel 902 to enable pressure measurements of different sections of the chamber to be made. The chamber may comprise cross-sections of different areas to enable rheological measurements to be made from the pressure measurements during actuation of plungers 360, 460. The actuation of plungers 360, 460 leads to varying flow rates and pressures within the channel 902. Plungers 360, 460 may therefore act as syringe pumps. Provided the pressures are less than the leakage pressure limit, liquids will remain within the channel, and provided the magnitude of the negative pressures are less than the magnitude of the back-flow pressure limit, gas will not enter the channel 902.

The fluid system 900 may further comprise an automated motion control system (not shown) configured to engage the plungers 360, 460 to control the movement of (actuate) the plungers 360, 460. For example, the automated motion control system may control reciprocating movement of the plungers 360, 460.

The absence of moving parts in the fluid-check valves 310, 410 of the plungers 360, 460 may also advantageously reduce the time required to vent gas from the fluid conduit 901 with micro-fluidic dimensions (e.g. <about 3 mm). This is particularly important for rheological applications involving blood related fluids to limit coagulation and/or clotting of the blood where the maximum time allowed to inject samples, vent gas and conduct measurements may be about 30 seconds. The fluid check-valves 310, 410 may, for example, require less than about 10 seconds to vent gas from the fluid conduit 101.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A self-sealing venting fluidic system comprising:
    a fluid conduit comprising an inner serface;
    a fluid check-valve for venting gas from the fluidic system, the fluid check-valve comprising:
        a retention body defining a fluid aperture having an upstream side and a downstream side;
        a hydrophilic porous material held by the retention body and disposed to cover the fluid aperture;
        a hydrophobic porous material held by the retention body and disposed to cover the fluid aperture and adjacent the hydrophilic porous material,
    wherein one face of the hydrophilic porous material is in fluid communication with the upstream side of the aperture, and one face of the hydrophobic porous material is in fluid communication with the downstream side of the aperture,
    wherein the hydrophilic porous material is configured to retain liquid from the upstream side to hinder passage of gas from the downstream side to the upstream side, and the hydrophobic porous material is configured to hinder passage of liquid from the upstream side to the downstream side, and
    wherein the fluid check-valve is fitted within the fluid conduit and forms a fluidic seal with the inner surface of the fluid conduit to separate the fluid conduit into an upstream side to contain a gas and a liquid, and a downstream side to receive the gas; and
    a plunger adapted to fit within the fluid conduit, wherein the plunger comprises the fluid check-valve.

2. The fluidic system according to claim 1, wherein the hydrophilic porous material is disposed upstream of the hydrophobic porous material.

3. The fluidic system of claim 1, wherein at least one of the hydrophilic porous material and the hydrophobic porous material define a plurality of pores, and the plurality of pores have a median pore diameter in the range of about 0.1 microns to about 10 microns.

4. The fluidic system according to claim 3, wherein the plurality of pores have a median pore diameter less than about 1 micron.

5. The fluidic system according to claim 1, wherein the hydrophobic porous material and the hydrophilic porous material directly contact each other.

6. The fluid fluidic system according to claim 1, wherein the hydrophobic porous material and the hydrophilic porous material are spaced from each other.

7. The fluidic system according to claim 6, wherein the hydrophobic porous material and the hydrophilic porous material are spaced from each other by a distance greater than about 0 mm and less than about 2 mm.

8. The fluidic system according to claim 6, wherein the hydrophobic porous material and the hydrophilic porous material are separated by a material that allows the passage or transmission of fluid.

9. The fluidic system according to claim 6, wherein the hydrophobic porous material and the hydrophilic porous material are separated by a void.

10. The fluidic system according to claim 1, wherein the retention body comprises a first part and a second part, wherein the first part and second part are coupled together to cooperatively retain the hydrophilic porous material and the hydrophobic porous material.

11. The fluidic system of claim 10, wherein one of the first part and second part is shaped to define a recess and a section of the other of the first and second parts is shaped to fit within the recess such that the first part and second part are coupled together.

12. The fluidic system of claim 11, wherein the first part and second part are: shaped to form a friction fit, or bonded together.

13. The fluidic system according to claim 11, wherein the recess has a size that is tapered along a depth of the recess.

14. The fluidic system according to claim 11, wherein at least a section of each of the hydrophilic porous material and the hydrophobic porous material are located within the recess.

15. The fluidic system according to claim 10, wherein the first part comprises an upstream surface in fluid connection with the upstream side that has at least a portion of a frustoconical or a concave shape to assist passage of gas from the upstream side to the downstream side.

16. The fluidic system according to claim 1, wherein if the hydrophilic porous material has been exposed to a liquid, the fluid check-valve hinders the passage of gas from the downstream side to the upstream side with a backflow pressure limit of about −80 kPa.

17. The fluidic system according to claim 1, wherein the hydrophobic porous material is configured to hinder the passage of liquid from the upstream side to the downstream side with a leakage pressure limit of about 150 kPa.

18. The fluidic system according to claim 1, wherein the fluid conduit defines a plurality of ports in fluid communication with the upstream side to enable pressure measurements to be performed.

19. The fluidic system according to claim 1, wherein the fluid conduit defines an inlet in fluid communication with the upstream side to enable fluids to be injected into the upstream side.

20. The fluidic system according to claim 1, further comprising an automated motion control system configured to engage the plunger to control the movement of the plunger.

21. The fluidic system according to claim 10, further comprising a baffle component located within the fluid conduit adjacent to the first part to promote liquid flow along the inner surface of the fluid conduit.

* * * * *